US008933301B2

(12) United States Patent  (10) Patent No.: US 8,933,301 B2
Hurst et al.  (45) Date of Patent: Jan. 13, 2015

(54) NON-TRANSGENIC TOMATO VARIETIES HAVING INCREASED SHELF LIFE POST-HARVEST DUE TO ALTERATIONS IN β-GALACTOSIDASE 4

(75) Inventors: Susan R. Hurst, Seattle, WA (US); Dayna L. Loeffler, Seattle, WA (US); Michael N. Steine, Kent, WA (US); Anna Amen, Redmond, WA (US); Dionne Vafeados, Snohomish, WA (US)

(73) Assignee: Arcadia Biosciences, Inc., Davis, CA (US)

( * ) Notice: Subject to any disclaimer, the term of this patent is extended or adjusted under 35 U.S.C. 154(b) by 554 days.

(21) Appl. No.: 12/976,995

(22) Filed: Dec. 22, 2010

(65) Prior Publication Data

US 2011/0159168 A1  Jun. 30, 2011

Related U.S. Application Data

(60) Provisional application No. 61/290,686, filed on Dec. 29, 2009.

(51) Int. Cl.
| | | |
|---|---|---|
| *C12N 15/05* | (2006.01) | |
| *A01H 5/00* | (2006.01) | |
| *A01H 1/06* | (2006.01) | |
| *A01H 5/08* | (2006.01) | |

(52) U.S. Cl.
CPC ... *A01H 5/08* (2013.01); *A01H 1/06* (2013.01)
USPC .......................... 800/284; 800/263; 800/317.4

(58) Field of Classification Search
None
See application file for complete search history.

(56) References Cited

U.S. PATENT DOCUMENTS

| 5,994,075 | A | 11/1999 | Goodfellow |
|---|---|---|---|
| 6,872,813 | B1 | 3/2005 | Gross |
| 2004/0053236 | A1 | 3/2004 | McCallum |
| 2005/0014267 | A1 | 1/2005 | Gross |
| 2005/0120418 | A1* | 6/2005 | Fuerstenberg et al. ....... 800/287 |

OTHER PUBLICATIONS

Smith et al 2002. Down-regulation of tomato beta-galactosidase 4 results in decreased fruit softening. Plant Phys. 129:1755-1762.*
Shehata et al 2007. Attitudes of Hawai'i consumers toward genetically modified fruit. UH-CTAHR. BIO-7:1-8.*
Cantwell et al. 2002. Report to the California Tomato Commission tomato variety trials: Postharvest evaluations for 2001. p. 1-11.*
Alba, Plant Physiology 123:363-370, 2000.
Cantwell, Report to the California Tomato Commission: Tomato Variety Trials: Postharvest Evaluations for 2001.
Chen, A Rapid DNA Minipreparation Method Suitable for AFLP and Other PCR Applications, Plant Molecular Biology Reporter 17: 53-57, 1999.
Colbert, High-Throughput Screening for Induced Point Mutations, Plant Physiology 126:480-484, 2001.
Edan, Color and Firmness Classification of Fresh Market Tomatoes, Journal of Food Science 62(4): 793-796, 1997.
Errington, Changes in the Force Relaxation and Compression Responses of Tomatoes During Ripening: the Effect of Continual Testing and Polygalacturonase Activity, Postharvest Biology and Technology 11:141-147, 1997.
Henikoff, Using Substitution Probabilities to Improve Position-Specific Scoring Matrices, Computer Applications in the Biosciences 12:135-143, 1996.
Innis, PCR Protocols: A Guide to Methods and Applications, Academic Press, San Diego, 1990.
Lesage, Measurement of Tomato Firmness by Using a Non-Destructive Mechanical Sensor, Postharvest Biology and Technology 8:45-55, 1996.
Li, Integrated platform for detection of DNA Sequence Variants Using Capillary Array Electrophoresis, Electrophoresis 23(10):1499-1511, 2002.
Malundo, Flavor Quality of Fresh Tomato (Lycopersicon esculentum Mill.) as Affected by Sugar and Acid Levels, Postharvest Biology and Technology 6:103-110, 1995.
McCallum, Target Screening for Induced Mutations, Nature Biotechnology 18:455-457, 2000a.
McCallum, Targeting Induced Local Lesions n Genomes (TILLING) for Plant Functional Genomics, Plant Physiology 123:439-442, 2000b.
Moctezuma, Antisense Suppression of a β-Galactosidase Gene (TBG6) in Tomato Increases Fruit Cracking, Journal of Experimental Botany 54(390):2025-2033, 2003.
Ng, SIFT: Predicting Amino Acid Changes that Affect Protein Function, Nucleic Acids Research 31(13):3812-3814, 2003.
Smith, A Family of at Least Seven β-Galactosidase Genes Is Expressed During Tomato Fruit Development, Plant Physiology 123:1173-1183, 2000.
Smith, Down-Regulation of Tomato β-Galactosidase 4 Results in Decreased Fruit Softening, Plant Physiology 129, 1755-1762, 2002.
Stewart, A Rapid CTAB DNA Isolation Technique Useful for RAPD Fingerprinting and Other PCR Applications, Bio Techniques 14(5):748-749, 1993.
Taylor, Parsensp: A Tool for the Analysis of Nucleotide Polymorphisms, Nucleic Acids Research 31:3808-3811, 2003.

* cited by examiner

*Primary Examiner* — Anne Kubelik
*Assistant Examiner* — Jeffrey Bolland

(57) ABSTRACT

The present invention provides a series of independent human-induced, non-transgenic mutations found in at least one tomato β-galactosidase 4 gene, tomato plants having these mutations in at least one of their tomato β-galactosidase 4 genes, and a method of creating and identifying similar and/or additional mutations in the tomato β-galactosidase 4 gene by screening pooled and/or individual tomato plants. Tomato plants identified and produced in accordance with the present invention have fruit that are firmer when ripe with reduced post-harvest softening compared to fruit from wild type tomato plants as a result of non-transgenic mutations in at least one of their tomato β-galactosidase 4 genes.

9 Claims, No Drawings

US 8,933,301 B2

NON-TRANSGENIC TOMATO VARIETIES HAVING INCREASED SHELF LIFE POST-HARVEST DUE TO ALTERATIONS IN β-GALACTOSIDASE 4

CROSS-REFERENCE TO RELATED APPLICATIONS

This application claims priority to U.S. Provisional Application No. 61/290,686, filed on Dec. 29, 2009, which is hereby incorporated, in its entirety, by reference herein.

STATEMENT REGARDING FEDERALLY SPONSORED RESEARCH OR DEVELOPMENT

This invention was made with government support under United States Department of Defense Contract Nos. W911QY-05-C-0038 and W911QY-07-C-0121. The government has certain rights in this invention.

FIELD OF THE INVENTION

This invention relates to novel human-induced, non-transgenic mutations of the tomato β-galactosidase 4 gene and tomato plants having such non-transgenic mutations in at least one of their tomato β-galactosidase 4 gene sequences. This invention further relates to tomatoes that are firmer when ripe and soften more slowly post-harvest than wild type tomatoes as a result of human-induced, non-transgenic mutations in at least one of their tomato β-galactosidase 4 genes. This invention also relates to a method that utilizes non-transgenic means to create tomatoes having mutations in at least one of their tomato β-galactosidase 4 genes.

BACKGROUND

One of the main challenges facing today's tomato industry is how to deliver to a processing plant or to the marketplace tomato fruit that have been vine-ripened (and thus are desirable to consumers in terms of taste, texture, and color), but that remain firm without the usual post-harvest ripening-related softening that reduces shelf life of harvested fruit. Using traditional breeding methods, which are very labor intensive, it could take years to develop a novel tomato variety that ultimately may display only a modest increase in shelf life. Instead, recent studies have utilized genetic and biochemical techniques in an effort to identify the factors that regulate fruit ripening. By identifying and modifying the expression of specific genes, researchers and breeders hope to develop new tomato varieties that have the desirable qualities of vine-ripened fruit, but that are resistant to post-harvest softening and therefore display an extended shelf life.

Fruit softening is one of the many ripening-related changes—including alterations in fruit texture, color, aroma, and metabolism of sugars and organic acids—that occur as a result of a developmental program triggered by ethylene. The changes associated with ripening, in particular post-harvest softening, limit the shelf life of fresh produce, such as tomatoes. Several genes associated with the ripening process in tomato have been identified and include at least seven members of a family of genes called the β-galactosidase genes (Smith and Gross, Plant Physiology 123:1173-1184, 2000).

β-galactosidases comprise a family of genes that catalyze the hydrolysis of terminal galactosyl residues from carbohydrates, glycoproteins, and galactolipids. One family member, tomato β-galactosidase 4 (TBG4), codes for the enzyme β-galactosidase II, which has been proposed to play a role in cell wall degradation that underlies fruit softening.

Consistent with this idea, antisense down-regulation of TBG4 was reported to increase tomato fruit firmness by up to 40% compared to control fruit (Smith et al., Journal of Experimental Botany 54(390):2025-2033, 2002). Though the authors concluded that the "presence of the TBG4 antisense construct is linked to significantly firmer fruit in four of the six antisense lines" they went on to state that "there are no clear correlations linking the biochemical data to the increased firmness among all the antisense lines when compared with control." Further, data presented by Smith et al. in FIGS. 1 and 2 fail to confirm the efficacy of their TBG4 antisense construct. Not only were the authors unable to replicate the suppression of TBG4 mRNA levels that they first observed in fruit from line 1-1 at breaker plus 3 days (B3) (see FIG. 1) in a second study (FIG. 2), they reported that TBG4 mRNA levels were unexpectedly more abundant in fruit from four antisense lines than in parental control fruit at breaker plus 7 days (B7). These expression data show that the antisense construct did not constitutively suppress TBG4 expression as the authors expected. Because TBG4 cDNA shares approximately 70% nucleotide sequence identity to other β-galactosidase gene family members, Smith et al. examined expression of several TBG genes in fruit from line 1-1 to evaluate the specificity of their antisense suppression. Compared to parental control fruit, TBG3 mRNA levels in fruit from line 1-1 were significantly lower at mature green and significantly higher at B3 and B7. Taken together, these observations raise the possibility that the alterations Smith et al. observed in fruit firmness were not the result of antisense suppression of TBG4 mRNA expression. Because there are no characterized mutations of the TBG4 gene in tomato, the role of this gene in fruit firmness has not been assessed using an independent approach that specifically targets the TBG4 gene. The method described herein, in contrast to antisense technology, can be used to specifically target the TBG4 gene despite its high identity with other family members.

Transgenic approaches targeting the TBG4 gene have been proposed to modify β-galactosidase gene expression and β-galactosidase II protein expression during tomato fruit development (U.S. Pat. No. 6,872,813; U.S. Patent Publication No. 20050014267 A1). However, public acceptance of genetically modified plants, particularly with respect to plants used for food, is not universal. Since many consumers have clear preferences against genetically modified foods, it would be useful to have a tomato exhibiting reduced levels of TBG4 that was not the result of genetic engineering methods. A cultivated tomato that is firmer when ripe and has reduced post-harvest fruit softening as a result of altered TBG4 protein that is not the result of genetic engineering would have tremendous value for the tomato industry, including fresh market and processor tomatoes. Such a tomato could be used in a variety of tomato food products for example, sliced tomatoes, canned tomatoes, ketchups, soups, sauces, juices and pastes.

To date, mutations in the TBG4 gene of tomato have not been reported and no one has reported or described a naturally occurring "knockout" or "knockdown" of TBG4. Therefore, the effect of "knockout" or "knockdown" of TBG4 on tomato fruit firmness is not known. It would be useful to have an allelic series of mutations in the TBG4 gene that provide a spectrum of phenotypes that could be used to optimize the breeding tomato varieties that retain many of the quality traits of vine-ripened tomatoes, yet have an extended shelf life. Tomato lines with TBG4 mutations that have been genetically characterized could also be crossed with lines that carry mutations in other genes involved in ripening. A cultivated tomato that is firmer and has reduced post-harvest softening as a result of its TBG4 gene being either knocked out or otherwise hindered that is not the result of genetic engineering would not only confirm the importance of this particular β-galactosidase gene in tomato fruit softening, but would have tremendous value for the entire tomato industry.

SUMMARY OF THE INVENTION

In accordance with one exemplary embodiment, the present invention includes a tomato plant having tomato fruit that are firmer when ripe and soften more slowly post-harvest than wild type tomato fruit, due to a human-induced, non-transgenic mutation in at least one of the TBG4 genes, as well as fruit, seeds, pollen, plant parts and progeny of that plant.

In accordance with another exemplary embodiment, the present invention includes food and food products incorporating tomato fruit having increased firmness, reduced post-harvest softening and increased shelf life post-harvest as a result of having a human-induced non-transgenic mutation in at least one TBG4 gene.

In accordance with yet another exemplary embodiment, the present invention includes a method of identifying and producing a tomato plant having fruit with increased firmness as compared to wild type tomato fruit comprising the steps of obtaining plant material from a parent tomato plant, inducing at least one mutation in at least one TBG4 gene of the plant material by treating the plant material with a mutagen to create mutagenized plant material, culturing the mutagenized plant material to produce progeny tomato plants, analyzing progeny tomato plants to detect at least one mutation in at least one TBG4 gene, selecting progeny tomato plants that have fruit with extended shelf life compared to the parent tomato plant; and repeating the cycle of culturing the progeny tomato plants to produce additional progeny plants having extended shelf life.

BRIEF DESCRIPTION OF THE SEQUENCE LISTING

SEQ ID NO: 1 shows a *Lycopersicum esculentum* β-galactosidase (TBG4) mRNA, complete cds (NCBI Accession Number AF020390).

SEQ ID NOs: 2-18 show PCR primers of the present invention that were useful for identifying a partial genomic sequence for TBG4.

SEQ ID NOs: 19-21 show parts one, two and three of a partial genomic sequence for *Lycopersicum esculentum* β-galactosidase (TBG4).

SEQ ID NO: 22 shows the protein encoded by SEQ ID NO: 1 (NCBI Accession Number AAC25984).

SEQ ID NOs: 23-28 show the DNA sequences for the *Lycopersicum esculentum* β-galactosidase 4 (TBG4)-specific PCR primers used to detect the mutations of the present invention.

DETAILED DESCRIPTION OF EXEMPLARY EMBODIMENTS

In accordance with one exemplary embodiment, the present invention provides tomatoes that are firmer when ripe and soften more slowly post harvest as compared to wild type tomatoes due to a mutation in at least one of their TBG4 genes and without the inclusion of foreign nucleic acids in the tomatoes' genomes. In accordance with other exemplary embodiments, the present invention provides a series of independent non-transgenic mutations in the TBG4 gene; tomatoes having these mutations in at least one of their TBG4 genes; and a method of creating and identifying similar and/or additional mutations in the TBG4 gene of tomatoes.

In order to create and identify the TBG4 mutations and tomatoes of the present invention, the present inventors utilized a method known as TILLING. See McCallum et al., Nature Biotechnology 18:455-457, 2000; McCallum et al., Plant Physiology 123:439-442, 2000; Colbert et al., Plant Physiology 126:480-484, 2001; U.S. Pat. No. 5,994,075 and U.S. Patent Publication No. 20040053236 A1, all of which are incorporated herein by reference. In the basic TILLING methodology, plant material, such as seed, is subjected to chemical mutagenesis, which creates a series of mutations within the genomes of the seeds' cells. The mutagenized seeds are grown into adult M1 plants and self-pollinated. DNA samples from the resulting M2 plants are pooled and are then screened for mutations in a gene of interest. Once a mutation is identified in a gene of interest, the seeds of the M2 plant carrying that mutation are grown into adult M3 plants and screened for the phenotypic characteristics associated with the gene of interest.

Any cultivar of tomato having at least one TBG4 gene that has a coding sequence with substantial identity to SEQ ID NO: 1 may be used in accordance with the present invention. As used herein, "substantial identity" means that the DNA sequence of the gene has a coding sequence that is sufficiently similar to SEQ ID NO: 1 at the nucleotide level to code for the equivalent protein as SEQ ID NO: 1, allowing for allelic differences between cultivars. Though estimated to be fairly low in abundance, DNA polymorphisms exist between tomato cultivars and within tomato cultivars and these DNA polymorphisms may be silent with no effect on protein translation or they may affect translation and lead to changes in protein sequence. In accordance with one aspect of an exemplary embodiment of the invention, "substantial identity" may be present when the identity between the coding sequence of the TBG4 gene and SEQ ID NO: 1 is as low as about 85%, provided that the percent identity in the conserved regions is higher (e.g., at least about 90%). Preferably, the percent identity in the coding region is about 85-90%, more preferably about 90-95%, and optimally, it is above about 95%. One of skill in the art may prefer a tomato cultivar having commercial popularity or one having specific desired characteristics in which to create the TBG4-mutated tomatoes. Alternatively, one of skill in the art may prefer a tomato cultivar having few polymorphisms, such as an in-bred cultivar, in order to facilitate screening for mutations within the TBG4 locus.

In accordance with one exemplary embodiment of the present invention, seeds from tomatoes were mutagenized and then grown into M1 plants. The M1 plants were then allowed to self-pollinate and seeds from the M1 plant were grown into M2 plants, which were then screened for mutations in their TBG4 locus. While M1 plants may be screened for mutations, an advantage of screening the M2 plants is that all somatic mutations correspond to the germline mutations. One of skill in the art would recognize that a variety of tomato plant materials, including, but not limited to, seeds, pollen, plant tissue or plant cells, may be mutagenized in order to create the TBG4-mutated tomatoes in accordance with various embodiments of the present invention. However, the type of plant material mutagenized may affect when the plant DNA is screened for mutations. For example, when pollen is subjected to mutagenesis prior to pollination of a non-mutagenized plant, the seeds resulting from that pollination are grown into M1 plants. Every cell of the M1 plants will contain mutations created in the pollen, thus these M1 plants may then be screened for TBG4 mutations instead of waiting until the M2 generation.

Mutagens that create primarily point mutations and short deletions, insertions, transversions, and or transitions (about 1 to about 5 nucleotides), such as chemical mutagens or radiation, may be used to create mutations in accordance with the present invention. Mutagens conforming with the method of the present invention include, but are not limited to, ethyl methanesulfonate (EMS), methylmethane sulfonate (MMS), N-ethyl-N-nitrosurea (ENU), triethylmelamine (TEM), N-methyl-N-nitrosourea (MNU), procarbazine, chlorambucil, cyclophosphamide, diethyl sulfate, acrylamide monomer, melphalan, nitrogen mustard, vincristine, dimethylnitosamine, N-methyl-N'-nitro-Nitrosoguanidine (MNNG), nitrosoguanidine, 2-aminopurine, 7,12 dimethyl-benz(a)anthracene (DMBA), ethylene oxide, hexamethylphosphoramide, bisulfan, diepoxyalkanes (diepoxyoctane (DEO), diepoxybutane (BEB), and the like), 2-methoxy-6-chloro-9[3-(ethyl-2-chloro-ethyl)aminopropylamino]acridine dihydrochloride (ICR-170), and formaldehyde. Spontaneous mutations in TBG4 that may not have been directly caused by the mutagen can also be identified in accordance with various embodiments of the present invention.

Any suitable method of plant DNA preparation now known or hereafter devised may be used to prepare the tomato plant DNA for TBG4 mutation screening. For example, see Chen and Ronald, Plant Molecular Biology Reporter 17:53-57, 1999; Stewart and Via, Bio Techniques 14:748-749, 1993. Additionally, several commercial kits are available, including kits from Qiagen (Valencia, Calif.) and Qbiogene (Carlsbad, Calif.).

In accordance with one aspect of an exemplary embodiment of the invention, DNA samples from individual tomato plants are prepared and then pooled in order to expedite screening for mutations in TBG4 of the entire population of plants originating from the mutagenized plant tissue. The size of the pooled group may be dependent upon the sensitivity of the screening method used. In accordance with one aspect of an exemplary embodiment of the invention, groups of four or more individual tomato plants are pooled.

In accordance with another aspect of an exemplary embodiment, after the DNA samples are pooled, the pools are subjected to TBG4 sequence-specific amplification techniques, such as Polymerase Chain Reaction (PCR). For a general overview of PCR, see, e.g., PCR Protocols: A Guide to Methods and Applications (Innis, Gelfand, Sninsky, J., and White, eds.), Academic Press, San Diego, 1990. Any primer specific to the TBG4 locus or the sequences immediately adjacent to the TBG4 locus may be utilized to amplify the TBG4 sequences within the pooled DNA sample. Preferably, the primer is designed to amplify the regions of the TBG4 locus where useful mutations are most likely to arise. Most preferably, the primer is designed to detect mutations in the coding region of the TBG4 gene. Additionally, it is preferable for the primer to avoid known polymorphic sites in order to ease screening for point mutations. To facilitate detection of PCR products on a gel, the PCR primer may be labeled using any conventional or hereafter devised labeling method.

In accordance with one exemplary embodiment of the present invention, a partial genomic DNA sequence for the TBG4 gene was constructed. Based upon the previously published TBG4 complete cds. sequence GenBank Accession Number AF020390 (SEQ ID NO: 1), sets of primers (SEQ ID NOs: 2-18) were designed that amplified overlapping segments of tomato genomic DNA. PCR products were sequenced and a partial genomic DNA sequence composed of three parts with gaps of unknown length between them (SEQ ID NOs: 19-21) was deduced by aligning these overlapping segments. The protein encoded by SEQ ID NO: 1 is shown as SEQ ID NO: 22.

Exemplary primers (SEQ ID NOs: 2-18) that proved useful for identifying a partial genomic DNA sequence for TBG4 are shown below in Table 1. These primers are also detailed in the Sequence Listing appended hereto.

TABLE 1

Exemplary primers for identifying a partial genomic DNA sequence for TBG4.

| SEQ ID NO | PRIMER NAME | SEQUENCE |
| --- | --- | --- |
| 2 | TBG4seqL1 | ATTTGTTTATTGGATTTTTTTCTTCAGTGAAA |
| 3 | TBG4seqR1 | TGCTCTTTGTACCATTTTGATGAATCT |
| 4 | TBG4seqL2 | TATGCTGCGGTGACTAGTCTTGGAAGTAAT |
| 5 | TBG4seqR2 | GACGTTTTTCTGTTCCCATAGTCCGTT |
| 6 | TBG4seqL3 | TGGGTTCGAGGTTCACTAATGGCTCAAAAG |
| 7 | TBG4seqR3 | TCGGCGCGAATTCAAGCACCATAG |
| 8 | TBG4 1L | TGGGGGATTCCCTGTTTGGCTA |
| 9 | TBG4AR3 | TAATTTCATAAGCGGAGTTTAGGAAGTGTG |
| 10 | TBG4AR4 | ATATTCATCGAGAGGAGCATCATAATCGTAG |
| 11 | TBG4BL4 | TAATAAGCCTTACAAACCTAAAATGTGGACAG |
| 12 | TBG4CL3 | CAGAAGTTTTAATGTCTGCTTGTGTAATGCT |
| 13 | TBG4CR3 | ACCTAGAACTCCTGCATTCCATGTATCATAA |
| 14 | TBG4BR5 | TATCAAATTGCTTACCACAGGATCAGGAGCAT |
| 15 | TBG4_FL1 | CTCCACATCTGCATAACACAGAACGGAAAT |
| 16 | TBG4_FR1 | CAAGCAGACATTAAAACTTCTGGCCCAAAT |
| 17 | TBG4IL1 | TTCCGTTGGTCTCCCGGTTAGTTTTCTATT |
| 18 | TBG4IR1 | GTTGCGTTTTGTTCGTCTGTGTGATCCTAT |

Exemplary primers (SEQ ID NOs: 23-28) that have proven useful in identifying useful mutations within the TBG4 sequence are shown below in Table 2. These primers are also detailed in the Sequence Listing appended hereto.

TABLE 2

PCR primers specific for the TBG4 gene in tomato.

| SEQ ID NO. | PRIMER SET | PRIMER NAME | SEQUENCE |
| --- | --- | --- | --- |
| 23 | TBG4F | TBG4F-3207 | CTCCACATCTGCATAACACAGAACGGAAAT |
| 24 | TBG4F | TBG4F-3208 | CAAGCAGACATTAAAACTTCTGGCCCAAAT |
| 25 | TBG4I | TBG4I-3213 | TTCCGTTGGTCTCCCGGTTAGTTTTCTATT |
| 26 | TBG4I | TBG4I-3214 | GTTGCGTTTTGTTCGTCTGTGTGATCCTAT |

TABLE 2-continued

PCR primers specific for the TBG4 gene in tomato.

| SEQ ID NO. | PRIMER SET | PRIMER NAME | SEQUENCE |
|---|---|---|---|
| 27 | TBG4J | TBG4J-3215 | CTACATTTAACGCGCCTGGAGGAAATGAT |
| 28 | TBG4J | TBG4J-3216 | CGCGAATTCAAGCACCATAGTTACTGAACA |

In accordance with one aspect of an exemplary embodiment of the invention, the PCR amplification products may be screened for TBG4 mutations using any method that identifies nucleotide differences between wild type and mutant sequences. Such methods may include, without limitation, sequencing, denaturing high pressure liquid chromatography (dHPLC), constant denaturant capillary electrophoresis (CDCE), temperature gradient capillary electrophoresis (TGCE) (see Li et al., Electrophoresis 23(10):1499-1511, 2002), or fragmentation using enzymatic cleavage, such as used in the high throughput method described by Colbert et al., Plant Physiology 126:480-484, 2001. Preferably, the PCR amplification products are incubated with an endonuclease that preferentially cleaves mismatches in heteroduplexes between wild type and mutant sequences. In accordance with another aspect of an exemplary embodiment, cleavage products are electrophoresed using an automated sequencing gel apparatus, and gel images are analyzed with the aid of a standard commercial image-processing program.

The present inventors have determined that to achieve reduced post-harvest softening in tomatoes, mutations that alter TBG4 function are desirable. Preferred mutations include missense, nonsense and splice junction changes, including mutations that prematurely truncate the translation of the TBG4 protein from messenger RNA, such as those mutations that create a stop codon within the coding regions of the TBG4 gene. Such mutations include insertions, repeat sequences, modified open reading frames (ORFs) and point mutations.

In accordance with yet another aspect of an exemplary embodiment of the invention, once an M2 plant having a mutated TBG4 sequence is identified, the mutation is analyzed to determine its effect on the expression, translation, and/or activity of the protein. In accordance with one exemplary embodiment, the PCR fragment containing the mutation is sequenced, using standard sequencing techniques, to determine the exact location of the mutation in relation to the overall TBG4 sequence. Each mutation is evaluated in order to predict its impact on protein function (i.e., completely tolerated to loss-of-function) using bioinformatics tools such as SIFT (Sorting Intolerant from Tolerant; Ng et al., Nucleic Acids Research 31:3812-3814, 2003), PSSM (Position-Specific Scoring Matrix; Henikoff and Henikoff, Computer Applications in the Biosciences 12:135-143, 1996), and PARSESNP (Taylor and Greene, Nucleic Acids Research 31:3808-3811, 2003). For example, a SIFT score that is less than 0.05 and/or a large change in PSSM score (e.g., roughly 10 or above) indicate a mutation that is likely to have a deleterious effect on protein function.

In accordance with a further aspect of an exemplary embodiment, if the initial assessment of a mutation in an M2 plant indicates it to be of a useful nature and in a useful position within the TBG4 gene, then further phenotypic analysis of the tomato plant containing that mutation is pursued. First, the M2 plant is backcrossed or outcrossed twice to create a BC1 plant in order to eliminate background mutations. Then the backcrossed or outcrossed BC1 plant is self-pollinated in order to create a BC1F2 plant that is homozygous for the TBG4 mutation. Tomatoes have diploid genomes—two homologous copies of each chromosome—and therefore two copies of the TBG4 gene. Fruit and plants that are heterozygous for the TBG4 mutation have the mutation in one copy of the TBG4 gene and the wild type allele in the other copy. Fruit and plants that are homozygous for the mutation have the mutation in both copies of the TBG4 gene. As used herein, wild type tomatoes are fruit that lack the TBG4 mutation and have two copies of the wild type allele. They are derived from plants that are heterozygous for the TBG4 mutation. Wild type sibling fruit are excellent controls as they have the same genetic background and have been subjected to the same growing conditions as the TBG4 mutant fruit, only they lack the TBG4 mutation.

In accordance with another aspect of an exemplary embodiment, several physical characteristics of the homozygous TBG4 mutant plants are assessed to determine if the mutation results in a useful phenotypic change in the tomato. Mutant TBG4 tomatoes are evaluated post-harvest for several traits, including rate of ripening, firmness, rot rate and shelf life compared to normal (e.g., wild type) parental tomatoes and/or to wild type sibling control tomatoes. Evaluations can be performed during storage. Examples of standard storage conditions include room temperature storage (approximately 68° F./20° C.) or refrigerated storage (approximately 55° F./13° C.). Normal fruit ripens on the vine or during storage such that the color of the tomato changes from light green to red. As this change occurs, the fruit tends to become softer, such that compression under a specified weight becomes greater and/or the force required to depress the surface of the fruit a specified distance becomes less. See Cantwell, Report to the California Tomato Commission: Tomato Variety Trials Postharvest Evaluations for 2001; Edan et al., J. Food Science 62(4): 793-796, 1997; Errington et al., Postharvest Biology and Technology 11: 141-147, 1997; Lesage and Destain, Postharvest Biology and Technology 8: 45-55, 1996. For lycopene measurements, see Alba et al., Plant Physiology 123:363-370, 2000.

The novel mutations identified in Table 3 are exemplary of the mutations created and identified according to various exemplary embodiments of the present invention.

TABLE 3

Examples of novel mutations created and identified in the tomato β-galactosidase 4 (TBG4) gene of tomato.

| Type of Mutation | Primer Set | EMS | Nucleotide Mutation According to SEQ ID NO: 1 | PSSM | SIFT | Amino Acid (a.a.) Mutation According to SEQ ID NO: 22 |
|---|---|---|---|---|---|---|
| Truncation | TBG4F | 1.2% | C1303T | Stop | Stop | Q414* |
| Severe missense | TBG4F | 1.2% | C1271T | 26.1 | 0 | P403L |
| Missense | TBG4J | 1.2% | A2156C | 9.6 | 0.07 | K698T |
| Severe missense | TBG4I | 1.2% | G1981A | 23.6 | 0 | G640R |

The nomenclature used in the Table 3 indicates the wild type nucleotide or amino acid, followed by its position according to the referenced SEQ ID NO, followed by the changed nucleotide or amino acid at that position using standard genetic code terminology (see specific examples below).

The following Examples are offered by way of illustration only, and not limitation. It is to be understood that the mutations below are merely exemplary and that similar mutations are also contemplated by the present invention.

EXAMPLE 1

Mutagenesis

In accordance with one exemplary embodiment of the present invention, tomato seeds of cultivars Shady Lady (hybrid) and NC84173 were vacuum infiltrated in $H_2O$ (approximately 1,000 seeds/100 ml $H_2O$ for approximately 4 minutes). The seeds were then placed on a shaker (45 rpm) in a fume hood at room temperature. The mutagen ethyl methanesulfonate (EMS) was added to the imbibing seeds to final concentrations ranging from about 0.1% to about 1.6% (v/v). Following a 6 to 24-hour incubation period, the EMS solution was replaced 4 times with fresh $H_2O$. The seeds were then rinsed under running water for approximately 1 hour. Finally, the mutagenized seeds were planted (96/tray) in potting soil and allowed to germinate indoors. Plants that were four to six weeks old were transferred to the field to grow to fully mature M1 plants. The mature M1 plants were allowed to self-pollinate and then seeds from the M1 plant were collected and planted to produce M2 plants.

DNA Preparation

DNA from the M2 plants produced in accordance with the above description was extracted and prepared in order to identify which M2 plants carried a mutation at their TBG4 locus. The M2 plant DNA was prepared using the methods and reagents contained in the Qiagen (Valencia, Calif.) DNeasy 96 Plant Kit. Approximately 50 mg of frozen plant sample was placed in a sample tube with a tungsten bead, frozen in liquid nitrogen, and ground 2 times for 1 minute each at 20 Hz using the Retsch Mixer Mill MM 300. Next, 400 µl of solution AP1 [Buffer AP1, solution DX and RNAse (100 mg/ml)] at 80° C. was added to the sample. The tube was sealed and shaken for 15 seconds. Following the addition of 130 µl Buffer AP2, the tube was shaken for 15 seconds. The samples were placed in a freezer at minus 20° C. for at least 1 hour. The samples were then centrifuged for 20 minutes at 5,600×g. A 400 µl aliquot of supernatant was transferred to another sample tube. Following the addition of 600 µl of Buffer AP3/E, this sample tube was capped and shaken for 15 seconds. A filter plate was placed on a square well block and 1 ml of the sample solution was applied to each well and the plate was sealed. The plate and block were centrifuged for 4 minutes at 5,600×g. Next, 800 µl of Buffer AW was added to each well of the filter plate, sealed and spun for 15 minutes at 5,600×g in the square well block. The filter plate was then placed on a new set of sample tubes and 80 µl of Buffer AE was applied to the filter. It was capped and incubated at room temperature for 1 minute and then spun for 2 minutes at 5,600×g. This step was repeated with an additional 80 µl Buffer AE. The filter plate was removed and the tubes containing the pooled filtrates were capped. The individual samples were then normalized to a DNA concentration of 5 to 10 ng/µl.

Tilling

The M2 DNA was pooled into groups of six individuals. The DNA concentration for each individual within the pool was 0.083 ng/µl, with a final concentration of 0.5 ng/µl for the entire pool. The pooled DNA samples were arrayed on microtiter plates and subjected to gene-specific PCR.

PCR amplification was performed in 15 µl volumes containing 2.5 ng pooled DNA, 0.75× ExTaq buffer (Panvera®, Madison, Wis.), 2.6 mM $MgCl_2$, 0.3 mM dNTPs, 0.3 µM primers, and 0.05 U Ex-Taq (Panvera) DNA polymerase. PCR amplification was performed using an MJ Research thermal cycler as follows: heat denaturation at 95° C. for 2 minutes; followed by 8 cycles of "touchdown PCR" (94° C. for 20 seconds, followed by an annealing step starting at 68-70° C. for 30 seconds and decreasing 1° C. per cycle, then a temperature ramp increasing 0.5° C. per second to 72° C., and followed by 72° C. for 1 minute); then 25-45 more cycles of PCR (94° C. for 20 seconds, 61-63° C. for 30 seconds, a ramp increasing 0.5° C. per second up to 72° C., 72° C. for 1 minute); and finally extension, denaturation and re-annealing steps (72° C. for 8 minutes; 98° C. for 8 minutes; 80° C. for 20 seconds; followed by 60 cycles of 80° C. for 7 seconds decreasing 0.3° C. per cycle).

The PCR primers (MWG Biotech, Inc., High Point, N.C.) were mixed as follows:

12.5 µl 100 µM IRD-700 (or alternatively, Cy5.5) labeled left primer 37.5 µl 100 µM left primer 5 µl 100 µM right primer 45 ul 100 µM IRD-800 labeled right primer The dye labels can be attached to either the right or left primer. In the present invention, the IRD labels were coupled to the oligonucleotide using conventional phosphoramidite chemistry.

PCR products (15 µl) were digested in 96-well plates. 30 µl of a solution containing 10 mM HEPES [4-(2-hydroxyethyl)-1-piperazineethanesulfonic acid] (pH 7.5), 10 mM $MgSO_4$, 0.002% (w/v) Triton X-100, 20 ng/ml of bovine serum albumin, and Surveyor Nuclease (Transgenomic, Inc.; 1:100,000 dilution) was added with mixing on ice, and the plate was incubated at 45° C. for 30 min. The specific activity of the Surveyor Nuclease was 800 units/µl, where a unit was defined by the manufacturer as the amount of enzyme required to produce 1 ng of acid-soluble material from sheared, heat denatured calf thymus DNA at pH 8.5 in one minute at 37° C. Reactions were stopped by addition of 10 µl of a 2.5 M NaCl solution with 0.5 mg/ml blue dextran and 75 mM EDTA, followed by the addition of 80 µl isopropanol. The reactions were precipitated overnight at room temperature and then spun at 4,000 rpm for 30 minutes in an Eppendorf Centrifuge 5810. Pellets were resuspended in 8 µl of 33% formamide with 0.017% bromophenol blue dye, heated at 80° C. for 7 minutes and then at 95° C. for 2 minutes. Samples were transferred to a membrane comb using a comb-loading robot (MWG Biotech). The comb was inserted into a slab acrylamide gel (6.5%), and electrophoresed for 4 hours at 1,500-V, 40-W, and 40-mA limits at 50° C.

During electrophoresis, the gel was imaged using a LI-COR (Lincoln, Nebr.) scanner, which has channels capable of detecting the IRD-700, and IRD-800 labels. The gel image showed sequence-specific pattern of background bands common to all 96 lanes. Rare events, such as mutations, create new bands that stand out above the background pattern. Plants with bands indicative of mutations of interest were evaluated by TILLING individual members of a pool mixed with wild type DNA and then sequencing individual PCR products. Plants carrying mutations confirmed by sequencing were grown up as described above (e.g., the M2 plant was backcrossed or outcrossed twice in order to eliminate background mutations and self-pollinated in order to create a plant that was homozygous for the mutation).

Physical and Biochemical Measurements

Tomatoes Selected for Study

Individual tomatoes selected for study were picked from plants derived from siblings of the same cross to preserve background phenotypes as much as possible. The plants and fruit were genotyped as homozygous for the mutation, heterozygous for the mutation, or wild type. Genotyping was performed using a cleaved amplified polymorphism sequence (CAPS) system to discriminate the three different alleles of the TBG4 locus. Basically, genomic DNA from plants of unknown genotype was amplified using primers TBG4F-3207 and TBG4F-3208 (SEQ ID NOs: 23 and 24). The PCR product was then digested with the restriction endonuclease BsgI. Because BsgI cuts wild type DNA at the mutation location but does not cut DNA that is homozygous for the mutation, genotypes were readily distinguishable when the digest products were run on a 1.5% agarose gel.

Measurement of Fruit Firmness

Fruit that were homozygous for the Q414* allele and their wild type sibling controls were harvested at the pink stage and allowed to ripen for three days at room temperature (68° F. or 20° C.) to the red stage when the first firmness test was taken. Tomatoes were considered to be at the pink stage when they had an a* value between 10 and 20 from the CIE L*a*b* color space measurements generated by a Minolta CR-400 Chromameter. Tomatoes were considered to be at the light red stage when they had a* values greater than 20. Tomatoes were stored for an additional six days at room temperature when the second firmness test was taken. Firmness was measured using a model TA-XT Texture Analyzer (Texture Technologies, Scarsdale, N.Y.). For each fruit firmness test, the amount of force required to depress the tomato fruit surface 5 mm was recorded at two equatorial fruit locations a quarter turn from each other. The two measurement locations for the first firmness test were marked on the fruit, so that the two subsequent measurements could be taken from uncompressed regions of the fruit. Thus, each fruit was depressed a total of four times. Pericarp firmness was measured by slicing the tomato fruit, removing the locules and taking measurements perpendicular to the internal surface of three slices for the first firmness test, and one or two slices for the second firmness test. The amount of force required to depress the tomato pericarp 3 mm was recorded for each pericarp sample. For analysis, firmness measurements from all slices for each fruit were averaged. Tomato fruit that were homozygous for the Q414* allele in TBG4 were significantly more firm when ripe than wild type control fruit and remained more firm when tested six days later. Exemplary data are shown in Table 4.

TABLE 4

Exemplary data from measurement of fruit firmness of tomatoes with the amino acid mutation Q414*. Data are expressed in Newtons.

| Test | Firmness Measure | Genotype | Sample Size | Firmness in Newtons (X ± SEM) | Significance by Two-tailed t-Test |
|---|---|---|---|---|---|
| First | Fruit | Homozygous | n = 20 | 19.6 ± 0.9 | p < 0.0001 |
|  |  | Wild type | n = 20 | 11.7 ± 0.3 |  |
|  | Pericarp | Homozygous | n = 1 | 30.8 |  |
|  |  | Wild type | n = 1 | 13.7 |  |
| Second | Fruit | Homozygous | n = 8 | 13.9 ± 1.0 | p < 0.0001 |
|  |  | Wild type | n = 10 | 8.1 ± 0.4 |  |
|  | Pericarp | Homozygous | n = 10 | 29.5 ± 4.0 | p < 0.016 |
|  |  | Wild type | n = 14 | 17.99 ± 2.5 |  |

Identification and Evaluation of the Amino Acid Mutation Q414*

DNA from a tomato originating from seeds of cultivar NC84173 that were incubated in 1.2% EMS was amplified using primer set TBGF (SEQ ID NOs: 23 and 24). The PCR amplification products were then incubated with Surveyor Nuclease (Transgenomic, Inc.) and electrophoresed. The electrophoresis gel image showed a fragment that stood out above the background pattern for the PCR amplification products. Therefore, it was likely that this fragment contained a heteroduplex created by a mutation in a TBG4 sequence. Sequence analysis of this fragment showed the mutation was a cytosine (C) to thymine (T) change at nucleotide 1303 of SEQ ID NO: 1. This mutation correlates with a change from glutamine at amino acid 414 of the TBG4 protein (SEQ ID NO: 22) to a stop codon (*). Tomatoes homozygous for the Q414* mutation in TBG4 are significantly firmer when ripe than wild type sibling control tomatoes and soften more slowly post-harvest. Since post-harvest softening is one of the major factors that negatively affects shipping and handling of tomatoes and reduces their shelf life, the Q414* mutation in at least one TBG4 gene would be useful for breeding tomatoes with improved quality and commercial value.

The above examples are provided to illustrate exemplary embodiments of the present invention but not limit its scope. Other variants of the invention will be readily apparent to one of ordinary skill in the art and are encompassed by the appended claims and all their equivalents. All publications, patents, and patent applications cited herein are hereby incorporated by reference.

INFORMAL SEQUENCE LISTING

SEQ ID NO: 1 shows a *Lycopersicum esculentum* β-galactosidase (TBG4) mRNA, complete cds (NCBI Accession Number AF020390).

```
  1 aaaaaaagtt tcaattttttt ttctaaaata aaaaaaaatt cattttttt gaatgtggaa 61 aaaatgctaa ggactaatgt gttgttgtta ttagttattt gtttattgga ttttttttct 121 tcagtgaaag ctagtgtttc ttatgatgac agagctataa tcataaatgg gaaaagaaaa 181 attcttattt ctggttcaat tcattatcca agaagcactc cacagatgtg gcctgatctt 241 atacaaaagg ctaaagatgg aggcttagat gttattgaaa cttatgttt ctggaatgga 301 catgagcctt ctcctggaaa atataatttt gaaggaagat atgatcttgt tagattcatc 361 aaaatggtac aaagagcagg actttatgtc aatttacgta ttggccctta cgtctgtgct 421 gaatggaact ttgggggatt ccctgtttgg ctaaaatatg tgcctggtat ggaatttaga 481 acaaacaatc agcctttaa ggtggctatg caaggatttg ttcagaaaat agtcaacatg
```

-continued

| INFORMAL SEQUENCE LISTING |
|---|
| 541  atgaagtcag aaaatttgtt tgaatctcaa ggaggaccaa taattatggc ccagatagaa |
| 601  aatgagtatg gaccagtaga atgggaaatt ggtgctcctg gtaaagctta tacaaaatgg |
| 661  gcagctcaaa tggctgtagg tttgaaaact ggtgtcccat ggatcatgtg taagcaagag |
| 721  gatgctcctg atcctgtgat tgatacttgt aatggcttct actgcgaagg gttccgtcct |
| 781  aataagcctt acaaacctaa aatgtggaca gaagtatgga ctggctggta tacgaaattc |
| 841  ggtggtccaa ttcctcaaag accagccgaa gacattgcat tttcagttgc caggtttgtt |
| 901  cagaacaatg gttcattctt caattactac atgtatcatg gaggaacaaa ttttggccgg |
| 961  acatcatcag ggcttttcat tgcaactagc tacgattatg atgctcctct cgatgaatat |
| 1021 gggttgctga atgaaccaaa gtatgggcac ttgagagact tacataaagc tatcaagcta |
| 1081 tctgaaccgg ctttagtttc atcatatgct gcggtgacta gtcttggaag taatcaagag |
| 1141 gctcatgttt atagatcaaa atctggagct tgtgctgctt ttttatccaa ctatgactct |
| 1201 agatattcag taaaagtcac ctttcagaat aggccataca atctgcctcc atggtccatc |
| 1261 agcattcttc ccgactgcaa aactgccgtt tacaacactg cacaggttaa ctctcaaagc |
| 1321 tcgagcataa agatgacgcc tgcaggtggt ggattgtctt ggcagtcata caatgaagaa |
| 1381 acgcctactg ctgatgacag cgatacactt acagctaacg gactatggga acagaaaaac |
| 1441 gtcacaagag attcatcaga ctatctgtgg tacatgacaa atgtaaatat agcatctaat |
| 1501 gaaggatttc taaagaacgg aaaggatcct tatctcactg ttatgtccgc tggtcatgtc |
| 1561 ttgcatgttt tcgtcaatgg aaaactatca ggaactgttt atggtacatt ggataatcca |
| 1621 aaacttacat acagtggcaa cgtgaagtta agagctggta ttaacaagat ttctctgctc |
| 1681 agtgtttccg ttggtctccc gaacgttggc gtgcattatg atacatggaa tgcaggagtt |
| 1741 ctaggtccag tcacgttgag cggtctcaat gaagggtcaa gaaacttggc gaaacagaaa |
| 1801 tggtcttaca aggttggtct gaaaggcgaa tcgttaagtc ttcactcctt aagtgggagt |
| 1861 tcttctgttg aatgggttcg aggttcacta atggctcaaa agcagcccct gacttggtac |
| 1921 aaggctacat ttaacgcgcc tggaggaaat gatccactag ctttagacat ggcaagtatg |
| 1981 ggaaaaggtc agatatggat aaatggtgaa ggcgtaggtc gccattggcc tggatacata |
| 2041 gcacaaggcg actgcagcaa atgcagttat gctggaacgt tcaacgagaa gaagtgccag |
| 2101 actaactgcg gacaaccttc tcagagatgg taccatgttc cacgatcgtg gctgaaacca |
| 2161 agtggaaact tgttagtagt attcgaagaa tggggaggta atccaacagg aatttctcta |
| 2221 gtcaggagat caagataaag aactcgaaaa gtaaaacttg ttcagtaact atggtgcttg |
| 2281 aattcgcgcc gaaaaataca tacacgaagc taacaatgga ggctacagtt tgcaaattgc |
| 2341 agctgaataa aacattagaa gataaagaaa tatttgatta aaaggagtat ataaatttac |
| 2401 agagaatttt ctttattctt tgtaaaactt tggtttataa agtttataca gaattttctg |
| 2461 ttatttggat tatgagattg aagaagattg tacagcttcc aaatactatt agaatacaaa |
| 2521 taaatttcat gt |
| SEQ ID NOs: 2-18 show PCR primers of the present invention useful for identifying a partial genomic sequence for TBG4 in tomato. |

| SEQ ID NO | PRIMER NAME | SEQUENCE |
|---|---|---|
| 2 | TBG4seqL1 | ATTTGTTTATTGGATTTTTTTCTTCAGTGAAA |
| 3 | TBG4seqR1 | TGCTCTTTGTACCATTTTGATGAATCT |

| | INFORMAL SEQUENCE LISTING | |
|---|---|---|
| 4 | TBG4seqL2 | TATGCTGCGGTGACTAGTCTTGGAAGTAAT |
| 5 | TBG4seqR2 | GACGTTTTTCTGTTCCCATAGTCCGTT |
| 6 | TBG4seqL3 | TGGGTTCGAGGTTCACTAATGGCTCAAAAG |
| 7 | TBG4seqR3 | TCGGCGCGAATTCAAGCACCATAG |
| 8 | TBG4 1L | TGGGGGATTCCCTGTTTGGCTA |
| 9 | TBG4AR3 | TAATTTCATAAGCGGAGTTTAGGAAGTGTG |
| 10 | TBG4AR4 | ATATTCATCGAGAGGAGCATCATAATCGTAG |
| 11 | TBG4BL4 | TAATAAGCCTTACAAACCTAAAATGTGGACAG |
| 12 | TBG4CL3 | CAGAAGTTTTAATGTCTGCTTGTGTAATGCT |
| 13 | TBG4CR3 | ACCTAGAACTCCTGCATTCCATGTATCATAA |
| 14 | TBG4BR5 | TATCAAATTGCTTACCACAGGATCAGGAGCAT |
| 15 | TBG4_FL1 | CTCCACATCTGCATAACACAGAACGGAAAT |
| 16 | TBG4_FR1 | CAAGCAGACATTAAAACTTCTGGCCCAAAT |
| 17 | TBG4IL1 | TTCCGTTGGTCTCCCGGTTAGTTTTCTATT |
| 18 | TBG4IR1 | GTTGCGTTTTGTTCGTCTGTGTGATCCTAT |

SEQ ID NO: 19 shows part one of a partial genomic sequence for
*Lycopersicum esculentum* β-galactosidase (TBG4).

aaaaaaagtttcaattttttttctaaaataaaaaaaaattcattttttttgaatgtggaaaaaatgcta
aggactaatgtgttgttgttattagttatttgtttattggattttttttcttcagtgaaagctagtgtt
tcttatgatgacagagctataatcataaatgggaaaagaaaaattcttatttctggttcaattcattat
ccaagaagcactccacaggtaaattatatacaaaaaaaattgtattatttcattattttcttgtttttg
gttgtaaagatcatttctttacactttgttatggattgtgtgaaatgggtgtgctttgtatttctgtaa
ttcttgtttttttaagaattttggttgtaaaaatgtgaactttatgcttttttatggcttctgtcaaaa
gggtctgttttgttttctgtaatttttaagtttcttctttatacattttaatggattcttagaaatg
ggtgtatcatgttttgtgtaattcttgttttttttaaaagcattttggttctaaaaatgcaaacttt
atgcttttttttatagcttctgtaaaaagggtgtgttttgttttctgtaatttttaagtttctaaaa
atcttttctttatacattttatgattctgtgaaatgggtttatcttgttttctgtaatacttgttt
agttatgatttttagttctaaaagtatgaactttacacttgttttctgtttatttaatgttttggtt
ctaaaaatcttttctttaccccttttcttataaacctatgcgattatgctgagtatgttattattgtgt
tttgcgttacttaagtcaaaggtatgtaggaaacaaaaggtaaaagaccctgcttatggaattgtact
ggatatgtcgttgttattattattgttgtttgtgttagttgagtcgagggtctatcgaagttatcctct
ctatcttcacttatgtacacgccacacttcctaaactccgcttatgaaattac SEQ ID NO: 20 shows part two of a partial genomic sequence for
*Lycopersicum esculentum* β-galactosidase (TBG4).

atgtggcctgatcttatacaaaaggctaaagatggaggcttagatgttattgaaacttatgttttctgg
aatggacatgagccttctcctggaaaatataattttgaaggaagatatgatatgttagattcatcaaaa
tggtacaaagagcaggactttatgtcaatttacgtattggcccttacgtctgtgctgaatggaactttg
ggggattccctgtttggctaaaatatgtgcctggtatggaatttagaacaaacaatcagccttttaagg
tggctatgcaaggatttgttcagaaaatagtcaacatgatgaagtcagaaaatttgtttgaatctcaag
gaggaccaataattatggcc

INFORMAL SEQUENCE LISTING

SEQ ID NO: 21 shows part three of a partial genomic sequence for *Lycopersicum esculentum* β-galactosidase (TBG4).

```
gggatacgactacgtacaccctacttgtggagttaaactggctatgatgttgatgttgttgttgttgca
gatagaaaatgagtatggaccagtagaatgggaaattggtgctcctggtaaagcttatacaaaatgggc
agctcaaatggctgtaggtttgaaaactggtgtcccatggatcatgtgtaagcaagaggatgctcctga
tcctgtggtaagcaatttgatataggacttgtttcaaggttcattttagacatctcatattgtcttgat
tgtgctacagattgatacttgtaatggcttctactgcgaagggttccgtcctaataagccttacaaacc
taaaatgtggacagaagtatggactggctggtaagtatcaagaacgcgaattacatgattctaatgcag
tttatgttcttctgagttggtttcttcattcaactactctatttagtcgaatgttcgttaatgatatac
tctctactatgctcaggtatacgaaattcggtggtccaattcctcaaagaccagccgaagacattgcat
tttcagttgccaggtttgttcagaacaatggttcattcttcaattactacatggtaagttagaacatct
ggttccgtgttcaagtttttctcgttaaacatggctattgtattgatgtactgtggttgcttcagtatc
atggaggaacaaattttggccggacatcatcagggcttttcattgcaactagctacgattatgatgctc
ctctcgatgaatatggtacgaaacaagaactagtattcttcttgtatctccacatctgcataacacaga
acggaaataatggaaaatttcctaaaaattattcatgcttgtcttgatgatttgcgttatggtgtaaaa
gggttgctgaatgaaccaaagtatgggcacttgagagacttacataaagctatcaagctatctgaaccg
gctttagtttcatcatatgctgcggtgactagtcttggaagtaatcaagaggttagtctgttttttttc
cctttgagtcgagggtctattggaagcagcctctctatctttaaggtaggggaaaggtttatgtatact
ctatcctctccagatcccactatgtgagactacactcgatatgttgttgtaattgtcgtgattttcctt
ctaacgctgtttacattttttttgaccaatataggctcatgtttatagatcaaaatctggagcttgtgc
tgcttttttatccaactatgactctagatattcagtaaaagtcacctttcagaataggccatacaatct
gcctccatggtccatcagcattcttcccgactgcaaaactgccgtttacaacactgcacaggtatagtt
taaataaataaataccgtcagtcctctctataaccgtcattctctatagcaacatttctctgtcatagt
ctatgtcatttgtggaaccgatctttcatgttaatgctatattatatgttttctataacaacacttttgc
tatagcagcccaaaagtactgaaacaaatgatgttgtaatgaggcagttatagagaggtttgactgtat
aagcatttgggccagaagttttaatgtctgcttgtgtaatgctgcaggttaactctcaaagctcgagca
taaagatgacgcctgcaggtggtggattgtcttggcagtcatacaatgaagaaacgcctactgctgatg
acagcgatacacttacagctaacggactatgggaacagaaaaacgtcacaagagattcatcagactatc
tgtggtacatgacaaagtgagtaacttacattttcctacttttttcgaatgattatatttagttccgtc
ttcactcacacatatctatatctaatatcataatgactttttttgttacttttttccagtgtaaatatag
catctaatgaaggatttctaaagaacggaaaggatccttatctcactgttatgtccgctggtcatgtct
tgcatgttttcgtcaatggaaaactatcaggtagcggaaacaacactattttgggattatggcaaatgc
ttttccctaacagactacttctctcagttccaatttgtctgacttgacacgaaatttaagaaagtaaag
tttgaatcttgtggccttaaacatgtcacgtggagtagagaacaaagagttgccctaaaaaaagaaaag
agacattcttttttgaaacggactagaaagggatagtaaaacaaacaaattgaaacggacagagtacatc
ttttgacgtctattcctgttttcctaacatctctttgtccttgaattgttgtaggaactgtttatggta
cattggataatccaaaacttacatacagtggcaacgtgaagttaagagctggtattaacaagatttctc
tgctcagtgtttccgttggtctcccggttagttttctatttcctgtttctccgatcctttattagcacc
gataaccaaacctttaaaaaaaaatataacctatggttttaactacatttcaaaacgttggcgtgcatt
```

INFORMAL SEQUENCE LISTING atgatacatggaatgcaggagttctaggtccagtcacgttgagcggtctcaatgaagggtcaagaaact
tggcgaaacagaaatggtcttacaaggtatgttaactaactaattgcttctcttctccccctaaagcct
gatcttcgtataactttgatatgcttttccttgagccgagggtctaccggaaacaacctctctacctcc
caagaccttacctgtgggattacactgcatatgttgttgttgatacctgaatagtctatactttgcttg
ttcataggttggtctgaaaggcgaatcgttaagtcttcactccttaagtgggagttcttctgttgaatg
ggttcgaggttcactagtggctcaaaagcagcccctgacttggtacaaggtaaattcctactggtataa
catcaacaaactacatatcaacacgtgtttatcgattatatgaagttgaatagcgtgtaacacatagtt
aacagactaacatacgttttccaggctacatttaacgcgcctggaggaaatgatccactagctttagac
atggcaagtatgggaaaaggtcagatatggataaatggtgaaggcgtaggtcgccattggcctggatac
atagcacaaggcgactgcagcaaatgcagttatgctggaacgttcaacgagaagaagtgccagactaac
tgcggacaaccttctcagagatggtaagcacatttccaacaacctttaacggagttataggatcacatg
aggtagaactacagtctgtatgcactctaccttccctagacctcattctgcgggaatacactgagtatg
ttgttgttgttccataggatcacacagacgaacaaaacgcaacatgtttgaagaaatgtgatactttttt
tttaccttcaacttgcattaagatacttcgcgaacttgtaaatttcaggtaccatgttccacgatcgtg
gctgaaaccaagtggaaacttgttagtagtattcgaagaatggggaggtaatccaacaggaatttctct
agtcaggagatcaagataaagaactcgaaaaggtatgcttttcgcctttgagaacactgattctgattc
aaaattatgtatatcacgtcgcgtctaaatcataaatttctgttaccattgtcttctactgtgacagta
aaacttgttcagtaactatggtgcttgaattcgcg SEQ ID NO: 22 shows the protein encoded by SEQ ID NO: 1 (NCBI Accession Number AAC25984).

ORIGIN

```
  1 mlrtnvllll viclldffss vkasysyddr aiiingkrki lisgsihypr stpqmwpdli
 61 qkakdggldv ietyvfwngh epspgkynfe grydlvrfik mvqraglyvn lrigpyvcae
121 wnfggfpvwl kyvpgmefrt nnqpfkvamq gfvqkivnmm ksenlfesqg gpiimagien
181 eygpveweig apgkaytkwa aqmavglktg vpwimckqed apdpvidtcn gfycegfrpn
241 kpykpkmwte vwtgwytkfg gpipqrpaed iafsvarfvq nngsffnyym yhggtnfgrt
301 ssglfiatsy dydapldeyg llnepkyghl rdlhkaikls epalvssyaa vtslgsnqea
361 hvyrsksgac aaflsnydsr ysvkvtfqnr pynlppwsis ilpdcktavy ntaqvnsqss
421 sikmtpaggg lswqsyneet ptaddsdtlt anglweqknv trdssdylwy mtnvniasne
481 gflkngkdpy ltvmsaghvl hvfvngklsg tvygtldnpk ltysgnvklr aginkislls
541 vsvglpnvgv hydtwnagvl gpvtlsglne gsrnlakqkw sykvglkges lslhslsgss
601 svewvrgslm aqkqpltwyk atfnapggnd plaldmasmg kgqiwingeg vgrhwpgyia
661 qgdcskcsya gtfnekkcqt ncgqpsqrwy hvprswlkps gnllvvfeew ggnptgislv
721 rrsr
```

SEQ ID NOs: 23-28 show PCR primers of the present invention specific for the TBG4 gene in tomato.

| SEQ ID. | NAME | SEQUENCE |
|---|---|---|
| 23 | TBG4F-3207 | CTCCACATCTGCATAACACAGAACGGAAAT |
| 24 | TBG4F-3208 | CAAGCAGACATTAAAACTTCTGGCCCAAAT |

-continued

| INFORMAL SEQUENCE LISTING | | | |
|---|---|---|---|
| 25 | TBG4I-3213 | TTCCGTTGGTCTCCCGGTTAGTTTTCTATT | |
| 26 | TBG4I-3214 | GTTGCGTTTTGTTCGTCTGTGTGATCCTAT | |
| 27 | TBG4J-3215 | CTACATTTAACGCGCCTGGAGGAAATGAT | |
| 28 | TBG4J-3216 | CGCGAATTCAAGCACCATAGTTACTGAACA | |

We claim:

1. A method of identifying a tomato plant that produces fruit that is firmer when ripe than fruit from wild type tomato plants, said method comprising the steps of:
   (a) obtaining plant material from a parent tomato plant;
   (b) treating said plant material with a mutagen to create mutagenized plant material;
   (c) culturing said mutagenized plant material to produce progeny tomato plants; and
   (d) analyzing said mutagenized plant material or said progeny tomato plants to identify a tomato plant having a human-induced, non-transgenic mutation in a tomato β-galactosidase 4 gene having a coding sequence with at least 85% identity to the coding sequence of SEQ ID NO:1, wherein said mutation is selected from the group consisting of C1271T, A2156C and G1981A, wherein the nucleotide change of said mutation is identified through the comparison to SEQ ID NO:1, and wherein said mutation, when expressed in the homozygous state in a tomato plant, causes said tomato plant to produce fruit that is firmer than fruit from wild type tomato plants not having said mutation when ripened at standard storage conditions.

2. The method of claim 1, wherein said mutation in a tomato β-galactosidase 4 gene codes for a protein comprising the amino acid change P403L and wherein said amino acid change is identified through the comparison to SEQ ID NO: 22.

3. The method of claim 1, wherein said mutation in a tomato β-galactosidase 4 gene codes for a protein comprising the amino acid change K698T and wherein said amino acid change is identified through the comparison to SEQ ID NO: 22.

4. The method of claim 1, wherein said mutation in a tomato β-galactosidase 4 gene codes for a protein comprising the amino acid change G640R and wherein said amino acid change is identified through the comparison to SEQ ID NO: 22.

5. A tomato fruit, a seed, a pollen grain, a plant part or a progeny of a tomato plant identified by the method of claim 1, wherein the fruit, the seed, the pollen grain, the plant part or the progeny comprises the human induced, non-transgenic mutation in the tomato β-galactosidase 4 gene.

6. A food or a food product incorporating the fruit of claim 5.

7. A method of producing a tomato plant having fruit that is firmer than fruit from a wild type tomato plant, said method comprising the steps of:
   (a) screening DNA from at least one tomato plant for mutations in a tomato β-galactosidase 4 gene having a coding sequence with at least 85% identity to the coding sequence of SEQ ID NO:1;
   (b) selecting a tomato plant having a mutation in said gene, wherein said mutation is selected from the group consisting of C1271T, A2156C, and G1981A and wherein the nucleotide change of said mutation is identified through comparison to SEQ ID NO:1;
   (c) self-pollinating, backcrossing or outcrossing said plant to produce additional progeny plants having said mutation; and
   (d) obtaining thereby a tomato plant capable of producing fruit that is firmer than fruit from wild type tomato plants not having said mutation.

8. A tomato fruit, a seed, a pollen gain, a plant part or a progeny of a tomato plant identified by the method of claim 7, wherein the fruit, the seed, the pollen grain, the plant part, or the progeny comprises the human induced, non-transgenic mutation in the tomato β-galactosidase 4 gene.

9. A food or a food product incorporating the fruit of claim 8.

* * * * *

SEQUENCE LISTING

<160> NUMBER OF SEQ ID NOS: 28

<210> SEQ ID NO 1
<211> LENGTH: 2532
<212> TYPE: DNA
<213> ORGANISM: Lycopersicon esculentum

<400> SEQUENCE: 1

```
aaaaaaagtt tcaattttttt ttctaaaata aaaaaaaatt catttttttt gaatgtggaa      60
aaaatgctaa ggactaatgt gttgttgtta ttagttattt gtttattgga ttttttttct     120
tcagtgaaag ctagtgtttc ttatgatgac agagctataa tcataaatgg aaaagaaaa      180
attcttattt ctggttcaat tcattatcca agaagcactc cacagatgtg gcctgatctt     240
atacaaaagg ctaaagatgg aggcttagat gttattgaaa cttatgtttt ctggaatgga     300
catgagcctt ctcctggaaa atataatttt gaaggaagat atgatcttgt tagattcatc     360
aaaatggtac aaagagcagg actttatgtc aatttacgta ttggccctta cgtctgtgct     420
gaatggaact ttgggggatt ccctgtttgg ctaaaatatg tgcctggtat ggaatttaga     480
acaaacaatc agccttttaa ggtggctatg caaggatttg ttcagaaaat agtcaacatg     540
atgaagtcag aaaatttgtt tgaatctcaa ggaggaccaa taattatggc ccagatagaa     600
aatgagtatg gaccagtaga atgggaaatt ggtgctcctg gtaaagctta tacaaaatgg     660
gcagctcaaa tggctgtagg tttgaaaact ggtgtcccat ggatcatgtg taagcaagag     720
gatgctcctg atcctgtgat tgatacttgt aatggcttct actgcgaagg gttccgtcct     780
aataagcctt acaaacctaa aatgtggaca gaagtatgga ctggctggta tacgaaattc     840
ggtggtccaa ttcctcaaag accagccgaa gacattgcat tttcagttgc caggtttgtt     900
cagaacaatg gttcattctt caattactac atgtatcatg gaggaacaaa ttttggccgg     960
acatcatcag ggctttttcat tgcaactagc tacgattatg atgctcctct cgatgaatat    1020
gggttgctga atgaaccaaa gtatgggcac ttgagagact acataaagc tatcaagcta    1080
tctgaaccgg ctttagtttc atcatatgct gcggtgacta gtcttggaag taatcaagag    1140
gctcatgttt atagatcaaa atctggagct tgtgctgctt ttttatccaa ctatgactct    1200
agatattcag taaaagtcac ctttcagaat aggccataca atctgcctcc atggtccatc    1260
agcattcttc ccgactgcaa aactgccgtt acaacactg cacaggttaa ctctcaaagc    1320
tcgagcataa agatgacgcc tgcaggtggt ggattgtctt ggcagtcata caatgaagaa    1380
acgcctactg ctgatgacag cgatacactt acagctaacg gactatggga acagaaaaac    1440
gtcacaagag attcatcaga ctatctgtgg tacatgacaa atgtaaatat agcatctaat    1500
gaaggatttc taaagaacgg aaaggatcct tatctcactg ttatgtccgc tggtcatgtc    1560
ttgcatgttt tcgtcaatgg aaaactatca ggaactgttg atggtacatt ggataatcca    1620
```

```
aaacttacat acagtggcaa cgtgaagtta agagctggta ttaacaagat ttctctgctc    1680
agtgtttccg ttggtctccc gaacgttggc gtgcattatg atacatgaa tgcaggagtt     1740 ctaggtccag tcacgttgag cggtctcaat gaagggtcaa gaaacttggc gaaacagaaa    1800
tggtcttaca aggttggtct gaaaggcgaa tcgttaagtc ttcactcctt aagtgggagt    1860
tcttctgttg aatgggttcg aggttcacta atggctcaaa agcagcccct gacttggtac    1920
aaggctacat ttaacgcgcc tggaggaaat gatccactag ctttagacat ggcaagtatg    1980
ggaaaaggtc agatatggat aaatggtgaa ggcgtaggtc gccattggcc tggatacata    2040
gcacaaggcg actgcagcaa atgcagttat gctggaacgt tcaacgagaa gaagtgccag    2100
actaactgcg acaaccttc tcagagatgg taccatgttc cacgatcgtg gctgaaacca     2160
agtggaaact tgttagtagt attcgaagaa tggggaggta atccaacagg aatttctcta    2220
gtcaggagat caagataaag aactcgaaaa gtaaaacttg ttcagtaact atggtgcttg    2280
aattcgcgcc gaaaaataca tacacgaagc taacaatgga ggctacagtt tgcaaattgc    2340
agctgaataa aacattagaa gataaagaaa tatttgatta aaaggagtat ataaatttac    2400
agagaatttt ctttattctt tgtaaaactt tggtttataa agtttataca gaattttctg    2460
ttatttggat tatgagattg aagaagattg tacagcttcc aaatactatt agaatacaaa    2520
taaatttcat gt                                                        2532
```

```
<210> SEQ ID NO 2
<211> LENGTH: 33
<212> TYPE: DNA
<213> ORGANISM: Artificial Sequence
<220> FEATURE:
<223> OTHER INFORMATION: Synthetic Construct

<400> SEQUENCE: 2
atttgtttat tggatttttt ttcttcagtg aaa                                 33

<210> SEQ ID NO 3
<211> LENGTH: 27
<212> TYPE: DNA
<213> ORGANISM: Artificial Sequence
<220> FEATURE:
<223> OTHER INFORMATION: Synthetic Construct

<400> SEQUENCE: 3
tgctctttgt accattttga tgaatct                                        27

<210> SEQ ID NO 4
<211> LENGTH: 30
<212> TYPE: DNA
<213> ORGANISM: Artificial Sequence
<220> FEATURE:
<223> OTHER INFORMATION: Synthetic Construct

<400> SEQUENCE: 4
tatgctgcgg tgactagtct tggaagtaat                                     30

<210> SEQ ID NO 5
<211> LENGTH: 27
<212> TYPE: DNA
<213> ORGANISM: Artificial Sequence
<220> FEATURE:
<223> OTHER INFORMATION: Synthetic Construct

<400> SEQUENCE: 5 gacgttttc tgttcccata gtccgtt                                         27
```

<210> SEQ ID NO 6
<211> LENGTH: 30
<212> TYPE: DNA
<213> ORGANISM: Artificial Sequence
<220> FEATURE:
<223> OTHER INFORMATION: Synthetic Construct

<400> SEQUENCE: 6
tgggttcgag gttcactaat ggctcaaaag        30

<210> SEQ ID NO 7
<211> LENGTH: 24
<212> TYPE: DNA
<213> ORGANISM: Artificial Sequence
<220> FEATURE:
<223> OTHER INFORMATION: Synthetic Construct

<400> SEQUENCE: 7
tcggcgcgaa ttcaagcacc atag        24

<210> SEQ ID NO 8
<211> LENGTH: 22
<212> TYPE: DNA
<213> ORGANISM: Artificial Sequence
<220> FEATURE:
<223> OTHER INFORMATION: Synthetic Construct

<400> SEQUENCE: 8
tgggggattc cctgtttggc ta        22

<210> SEQ ID NO 9
<211> LENGTH: 30
<212> TYPE: DNA
<213> ORGANISM: Artificial Sequence
<220> FEATURE:
<223> OTHER INFORMATION: Synthetic Construct

<400> SEQUENCE: 9
taatttcata agcggagttt aggaagtgtg        30

<210> SEQ ID NO 10
<211> LENGTH: 31
<212> TYPE: DNA
<213> ORGANISM: Artificial Sequence
<220> FEATURE:
<223> OTHER INFORMATION: Synthetic Construct

<400> SEQUENCE: 10
atattcatcg agaggagcat cataatcgta g        31

<210> SEQ ID NO 11
<211> LENGTH: 32
<212> TYPE: DNA
<213> ORGANISM: Artificial Sequence
<220> FEATURE:
<223> OTHER INFORMATION: Synthetic Construct

<400> SEQUENCE: 11
taataagcct tacaaaccta aaatgtggac ag        32

<210> SEQ ID NO 12
<211> LENGTH: 31
<212> TYPE: DNA
<213> ORGANISM: Artificial Sequence
<220> FEATURE:

<223> OTHER INFORMATION: Synthetic Construct

<400> SEQUENCE: 12
cagaagtttt aatgtctgct tgtgtaatgc t                              31

<210> SEQ ID NO 13
<211> LENGTH: 31
<212> TYPE: DNA
<213> ORGANISM: Artificial Sequence
<220> FEATURE:
<223> OTHER INFORMATION: Synthetic Construct

<400> SEQUENCE: 13
acctagaact cctgcattcc atgtatcata a                              31

<210> SEQ ID NO 14
<211> LENGTH: 32
<212> TYPE: DNA
<213> ORGANISM: Artificial Sequence
<220> FEATURE:
<223> OTHER INFORMATION: Synthetic Construct

<400> SEQUENCE: 14
tatcaaattg cttaccacag gatcaggagc at                             32

<210> SEQ ID NO 15
<211> LENGTH: 30
<212> TYPE: DNA
<213> ORGANISM: Artificial Sequence
<220> FEATURE:
<223> OTHER INFORMATION: Synthetic Construct

<400> SEQUENCE: 15
ctccacatct gcataacaca gaacggaaat                                30

<210> SEQ ID NO 16
<211> LENGTH: 30
<212> TYPE: DNA
<213> ORGANISM: Artificial Sequence
<220> FEATURE:
<223> OTHER INFORMATION: Synthetic Construct

<400> SEQUENCE: 16
caagcagaca ttaaaacttc tggcccaaat                                30

<210> SEQ ID NO 17
<211> LENGTH: 30
<212> TYPE: DNA
<213> ORGANISM: Artificial Sequence
<220> FEATURE:
<223> OTHER INFORMATION: Synthetic Construct

<400> SEQUENCE: 17
ttccgttggt ctcccggtta gttttctatt                                30

<210> SEQ ID NO 18
<211> LENGTH: 30
<212> TYPE: DNA
<213> ORGANISM: Artificial Sequence
<220> FEATURE:
<223> OTHER INFORMATION: Synthetic Construct

<400> SEQUENCE: 18
gttgcgtttt gttcgtctgt gtgatcctat                                30

```
<210> SEQ ID NO 19
<211> LENGTH: 1019
<212> TYPE: DNA
<213> ORGANISM: Lycopersicon esculentum

<400> SEQUENCE: 19
aaaaaaagtt tcaattttt ttctaaaata aaaaaaatt catttttttt gaatgtggaa      60
aaaatgctaa ggactaatgt gttgttgtta ttagttattt gtttattgga ttttttttct    120
tcagtgaaag ctagtgtttc ttatgatgac agagctataa tcataaatgg gaaagaaaa    180 attcttattt ctggttcaat tcattatcca agaagcactc cacaggtaaa ttatatacaa    240
aaaaaattgt attatttcat tatttttcttg tttttggttg taaagatcat ttctttacac   300
tttgttatgg attgtgtgaa atgggtgtgc tttgtatttc tgtaattctt gttttttaa     360 gaattttggt tgtaaaaatg tgaactttat gcttttttat ggcttctgtc aaagggtct    420 gttttgtttt tctgtaattt tttaagtttc ttctttatac attttaatgg attcttagaa    480
atgggtgtat catgttttg tgtaattctt gttttttttt aaaagcattt tggttctaaa    540
aatgcaaact ttatgctttt ttttatagct tctgtaaaaa gggtgtgttt gttttttctg    600
taatttttta agtttctaaa aatcttttct ttatacattt ttatggattc tgtgaaatgg    660
gtttatcttg tttttctgta atacttgttt agttatgatt tttagttcta aaagtatgaa    720
ctttacactt gtttttctgt ttatttaatg ttttggttc taaaaatctt ttctttaccc     780
ctttcttata aacctatgcg attatgctga gtatgttatt attgttgttt tgcgttactt    840
aagtcaaagg tatgtaggaa acaaaaggta aaaagaccct gcttatgaa ttgtactgga     900 tatgtcgttg ttattattat tgttgtttgt gttagttgag tcgagggtct atcgaagtta    960
tcctctctat cttcacttat gtacacgcca cacttcctaa actccgctta tgaaattac    1019

<210> SEQ ID NO 20
<211> LENGTH: 366
<212> TYPE: DNA
<213> ORGANISM: Lycopersicon esculentum

<400> SEQUENCE: 20
atgtggcctg atcttataca aaaggctaaa gatggaggct tagatgttat tgaaacttat     60
gttttctgga atggacatga gccttctcct ggaaaatata attttgaagg aagatatgat    120
cttgttagat tcatcaaaat ggtacaaaga gcaggacttt atgtcaattt acgtattggc    180
ccttacgtct gtgctgaatg gaactttggg ggattccctg tttggctaaa atatgtgcct    240
ggtatggaat ttagaacaaa caatcagcct tttaaggtgg ctatgcaagg atttgttcag    300
aaaatagtca acatgatgaa gtcagaaaat ttgtttgaat ctcaaggagg accaataatt    360
atggcc                                                                366

<210> SEQ ID NO 21
<211> LENGTH: 3761
<212> TYPE: DNA
<213> ORGANISM: Lycopersicon esculentum

<400> SEQUENCE: 21
gggatacgac tacgtacacc ctacttgtgg agttaaactg gctatgatgt tgatgttgtt     60
gttgttgcag atagaaaatg agtatggacc agtagaatgg gaaattggtg ctcctggtaa    120
agcttataca aaatgggcag ctcaaatggc tgtaggtttg aaaactgtg tcccatggat     180 catgtgtaag caagaggatg ctcctgatcc tgtggtaagc aatttgatat aggacttgtt    240
```

```
tcaaggttca ttttagacat ctcatattgt cttgattgtg ctacagattg atacttgtaa    300
tggcttctac tgcgaagggt tccgtcctaa taagccttac aaacctaaaa tgtggacaga    360
agtatggact ggctggtaag tatcaagaac gcgaattaca tgattctaat gcagtttatg    420
ttcttctgag ttggtttctt cattcaacta ctctatttag tcgaatgttc gttaatgata    480
tactctctac tatgctcagg tatacgaaat tcggtggtcc aattcctcaa agaccagccg    540
aagacattgc attttcagtt gccaggtttg ttcagaacaa tggttcattc ttcaattact    600
acatggtaag ttagaacatc tggttccgtg ttcaagtttt tctcgttaaa catgctatt     660
gtattgatgt actgtggttg cttcagtatc atggaggaac aaattttggc cggacatcat    720
cagggctttt cattgcaact agctacgatt atgatgctcc tctcgatgaa tatggtacga    780
aacaagaact agtattcttc ttgtatctcc acatctgcat aacacagaac ggaaataatg    840
gaaaatttcc taaaaattat tcatgcttgt cttgatgatt tgcgttatgg tgtaaaaggg    900
ttgctgaatg aaccaaagta tgggcacttg agagacttac ataaagctat caagctatct    960
gaaccggctt tagtttcatc atatgctgcg gtgactagtc ttggaagtaa tcaagaggtt   1020
agtctgtttt ttttcccttt gagtcgaggg tctattggaa gcagcctctc tatctttaag   1080
gtaggggaaa ggtttatgta tactctatcc tctccagatc ccactatgtg agactacact   1140
cgatatgttg ttgtaattgt cgtgattttt cttctaacgc tgtttacatt tttttttgacc  1200
aatataggct catgtttata gatcaaaatc tggagcttgt gctgctttt tatccaacta    1260
tgactctaga tattcagtaa aagtcacctt tcagaatagg ccatacaatc tgcctccatg   1320
gtccatcagc attcttcccg actgcaaaac tgccgtttac aacactgcac aggtatagtt   1380
taaataaata aataccgtca gtcctctcta taaccgtcat tctctatagc aacatttctc   1440
tgtcatagtc tatgtcattt gtggaaccga tctttcatgt taatgctata ttatatgttt   1500
tctataacaa cactttgcta tagcagccca aaagtactga aacaaatgat gttgtaatga   1560
ggcagttata gagaggtttg actgtataag catttgggcc agaagttta atgtctgctt    1620
gtgtaatgct gcaggttaac tctcaaagct cgagcataaa gatgacgcct gcaggtggtg   1680
gattgtcttg gcagtcatac aatgaagaaa cgcctactgc tgatgacagc gatacactta   1740
cagctaacgg actatgggaa cagaaaaacg tcacaagaga ttcatcagac tatctgtggt   1800
acatgacaaa gtgagtaact tacattttcc tactttttc gaatgattat atttagttcc    1860
gtcttcactc acacatatct atatctaata tcataatgac ttttttttgtt acttttttcca 1920
gtgtaaatat agcatctaat gaaggattc taaagaacgg aaaggatcct tatctcactg    1980
ttatgtccgc tggtcatgtc ttgcatgttt tcgtcaatgg aaaactatca ggtagcggaa   2040
acaacactat tttgggatta tggcaaatgc ttttccctaa cagactactt ctctcagttc   2100
caatttgtct gacttgacac gaaatttaag aaagtaaagt ttgaatcttg tggccttaaa   2160
catgtcacgt ggagtagaga acaaagagtt gccctaaaaa agaaaagag acattctttt    2220
tgaaacggac tagaaaggga tagtaaaaca aacaaattga aacggacaga gtacatcttt   2280
tgacgtctat tcctgttttc ctaacatctc tttgtccttg aattgttgta ggaactgttt   2340
atggtacatt ggataatcca aaacttacat acagtggcaa cgtgaagtta agagctggta   2400
ttaacaagat ttctctgctc agtgtttccg ttggtctccc ggttagtttt ctatttcctg   2460
tttctccgat cctttattag caccgataac caaaccttta aaaaaaaata taacctatgg   2520
ttttaactac atttcaaaac gttggcgtgc attatgatac atggaatgca ggagttctag   2580
gtccagtcac gttgagcggt ctcaatgaag ggtcaagaaa cttggcgaaa cagaaatggt   2640
```

-continued

```
cttacaaggt atgttaacta actaattgct tctcttctcc ccctaaagcc tgatcttcgt    2700
ataactttga tatgctttc cttgagccga gggtctaccg gaaacaacct ctctacctcc     2760 caagaccta cctgtgggat tacactgcat atgttgttgt tgatacctga atagtctata    2820
ctttgcttgt tcataggttg gtctgaaagg cgaatcgtta agtcttcact ccttaagtgg    2880
gagttcttct gttgaatggg ttcgaggttc actagtggct caaaagcagc ccctgacttg    2940
gtacaaggta aattcctact ggtataacat caacaaacta catatcaaca cgtgtttatc    3000
gattatatga agttgaatag cgtgtaacac atagttaaca gactaacata cgttttccag    3060
gctacattta acgcgcctgg aggaaatgat ccactagctt tagacatggc aagtatggga    3120
aaaggtcaga tatggataaa tggtgaaggc gtaggtcgcc attggcctgg atacatagca    3180
caaggcgact gcagcaaatg cagttatgct ggaacgttca acgagaagaa gtgccagact    3240
aactgcggac aaccttctca gagatggtaa gcacatttcc aacaaccttt aacggagtta    3300
taggatcaca tgaggtagaa ctacagtctg tatgcactct accttcccta gacctcattc    3360
tgcgggaata cactgagtat gttgttgttg ttccatagga tcacacagac gaacaaaacg    3420
caacatgttt gaagaaatgt gatactttt tttaccttca acttgcatta agatacttcg    3480
cgaacttgta aatttcaggt accatgttcc acgatcgtgg ctgaaaccaa gtggaaactt    3540
gttagtagta ttcgaagaat ggggaggtaa tccaacagga atttctctag tcaggagatc    3600
aagataaaga actcgaaaag gtatgctttt cgcctttgag aacactgatt ctgattcaaa    3660
attatgtata tcacgtcgcg tctaaatcat aaatttctgt taccattgtc ttctactgtg    3720
acagtaaaac ttgttcagta actatggtgc ttgaattcgc g                        3761
```

<210> SEQ ID NO 22
<211> LENGTH: 724
<212> TYPE: PRT
<213> ORGANISM: Lycopersicon esculentum

<400> SEQUENCE: 22

```
Met Leu Arg Thr Asn Val Leu Leu Leu Val Ile Cys Leu Leu Asp
1               5                   10                  15

Phe Phe Ser Ser Val Lys Ala Ser Val Ser Tyr Asp Asp Arg Ala Ile
                20                  25                  30

Ile Ile Asn Gly Lys Arg Lys Ile Leu Ile Ser Gly Ser Ile His Tyr
            35                  40                  45

Pro Arg Ser Thr Pro Gln Met Trp Pro Asp Leu Ile Gln Lys Ala Lys
        50                  55                  60

Asp Gly Gly Leu Asp Val Ile Glu Thr Tyr Val Phe Trp Asn Gly His
65                  70                  75                  80

Glu Pro Ser Pro Gly Lys Tyr Asn Phe Glu Gly Arg Tyr Asp Leu Val
                85                  90                  95

Arg Phe Ile Lys Met Val Gln Arg Ala Gly Leu Tyr Val Asn Leu Arg
            100                 105                 110

Ile Gly Pro Tyr Val Cys Ala Glu Trp Asn Phe Gly Gly Phe Pro Val
        115                 120                 125

Trp Leu Lys Tyr Val Pro Gly Met Glu Phe Arg Thr Asn Asn Gln Pro
    130                 135                 140

Phe Lys Val Ala Met Gln Gly Phe Val Gln Lys Ile Val Asn Met Met
145                 150                 155                 160

Lys Ser Glu Asn Leu Phe Glu Ser Gln Gly Gly Pro Ile Ile Met Ala
                165                 170                 175
```

-continued

```
Gln Ile Glu Asn Glu Tyr Gly Pro Val Glu Trp Glu Ile Gly Ala Pro
            180                 185                 190
Gly Lys Ala Tyr Thr Lys Trp Ala Ala Gln Met Ala Val Gly Leu Lys
        195                 200                 205
Thr Gly Val Pro Trp Ile Met Cys Lys Gln Glu Asp Ala Pro Asp Pro
210                 215                 220
Val Ile Asp Thr Cys Asn Gly Phe Tyr Cys Glu Gly Phe Arg Pro Asn
225                 230                 235                 240
Lys Pro Tyr Lys Pro Lys Met Trp Thr Glu Val Trp Thr Gly Trp Tyr
                245                 250                 255
Thr Lys Phe Gly Gly Pro Ile Pro Gln Arg Pro Ala Glu Asp Ile Ala
            260                 265                 270
Phe Ser Val Ala Arg Phe Val Gln Asn Asn Gly Ser Phe Phe Asn Tyr
        275                 280                 285
Tyr Met Tyr His Gly Gly Thr Asn Phe Gly Arg Thr Ser Ser Gly Leu
    290                 295                 300
Phe Ile Ala Thr Ser Tyr Asp Tyr Asp Ala Pro Leu Asp Glu Tyr Gly
305                 310                 315                 320
Leu Leu Asn Glu Pro Lys Tyr Gly His Leu Arg Asp Leu His Lys Ala
                325                 330                 335
Ile Lys Leu Ser Glu Pro Ala Leu Val Ser Ser Tyr Ala Ala Val Thr
            340                 345                 350
Ser Leu Gly Ser Asn Gln Glu Ala His Val Tyr Arg Ser Lys Ser Gly
        355                 360                 365
Ala Cys Ala Ala Phe Leu Ser Asn Tyr Asp Ser Arg Tyr Ser Val Lys
    370                 375                 380
Val Thr Phe Gln Asn Arg Pro Tyr Asn Leu Pro Pro Trp Ser Ile Ser
385                 390                 395                 400
Ile Leu Pro Asp Cys Lys Thr Ala Val Tyr Asn Thr Ala Gln Val Asn
                405                 410                 415
Ser Gln Ser Ser Ser Ile Lys Met Thr Pro Ala Gly Gly Gly Leu Ser
            420                 425                 430
Trp Gln Ser Tyr Asn Glu Glu Thr Pro Thr Ala Asp Asp Ser Asp Thr
        435                 440                 445
Leu Thr Ala Asn Gly Leu Trp Glu Gln Lys Asn Val Thr Arg Asp Ser
    450                 455                 460
Ser Asp Tyr Leu Trp Tyr Met Thr Asn Val Asn Ile Ala Ser Asn Glu
465                 470                 475                 480
Gly Phe Leu Lys Asn Gly Lys Asp Pro Tyr Leu Thr Val Met Ser Ala
                485                 490                 495
Gly His Val Leu His Val Phe Val Asn Gly Lys Leu Ser Gly Thr Val
            500                 505                 510
Tyr Gly Thr Leu Asp Asn Pro Lys Leu Thr Tyr Ser Gly Asn Val Lys
        515                 520                 525
Leu Arg Ala Gly Ile Asn Lys Ile Ser Leu Leu Ser Val Ser Val Gly
    530                 535                 540
Leu Pro Asn Val Gly Val His Tyr Asp Thr Trp Asn Ala Gly Val Leu
545                 550                 555                 560
Gly Pro Val Thr Leu Ser Gly Leu Asn Glu Gly Ser Arg Asn Leu Ala
                565                 570                 575
Lys Gln Lys Trp Ser Tyr Lys Val Gly Leu Lys Gly Glu Ser Leu Ser
            580                 585                 590
```

```
Leu His Ser Leu Ser Gly Ser Ser Val Glu Trp Val Arg Gly Ser
            595                 600                 605

Leu Met Ala Gln Lys Gln Pro Leu Thr Trp Tyr Lys Ala Thr Phe Asn
610                 615                 620

Ala Pro Gly Gly Asn Asp Pro Leu Ala Leu Asp Met Ala Ser Met Gly
625                 630                 635                 640

Lys Gly Gln Ile Trp Ile Asn Gly Glu Gly Val Gly Arg His Trp Pro
                645                 650                 655

Gly Tyr Ile Ala Gln Gly Asp Cys Ser Lys Cys Ser Tyr Ala Gly Thr
                660                 665                 670

Phe Asn Glu Lys Lys Cys Gln Thr Asn Cys Gly Gln Pro Ser Gln Arg
675                 680                 685

Trp Tyr His Val Pro Arg Ser Trp Leu Lys Pro Ser Gly Asn Leu Leu
690                 695                 700

Val Val Phe Glu Glu Trp Gly Gly Asn Pro Thr Gly Ile Ser Leu Val
705                 710                 715                 720

Arg Arg Ser Arg

<210> SEQ ID NO 23
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 23
ctccacatct gcataacaca gaacggaaat                                       30

<210> SEQ ID NO 24
<211> LENGTH: 30
<212> TYPE: DNA
<213> ORGANISM: Artificial Seuqnece
<220> FEATURE:
<223> OTHER INFORMATION: Synthetic Construct

<400> SEQUENCE: 24
caagcagaca ttaaaacttc tggcccaaat                                       30

<210> SEQ ID NO 25
<211> LENGTH: 30
<212> TYPE: DNA
<213> ORGANISM: Artificial Sequence
<220> FEATURE:
<223> OTHER INFORMATION: Synthetic DNA

<400> SEQUENCE: 25
ttccgttggt ctcccggtta gttttctatt                                       30

<210> SEQ ID NO 26
<211> LENGTH: 30
<212> TYPE: DNA
<213> ORGANISM: Artificial Sequence
<220> FEATURE:
<223> OTHER INFORMATION: Synthetic Construct

<400> SEQUENCE: 26
gttgcgtttt gttcgtctgt gtgatcctat                                       30

<210> SEQ ID NO 27
<211> LENGTH: 29
<212> TYPE: DNA
<213> ORGANISM: Artificial Sequence
```

```
<220> FEATURE:
<223> OTHER INFORMATION: Synthetic Construct

<400> SEQUENCE: 27
ctacatttaa cgcgcctgga ggaaatgat                                              29

<210> SEQ ID NO 28
<211> LENGTH: 30
<212> TYPE: DNA
<213> ORGANISM: Artificial Sequence
<220> FEATURE:
<223> OTHER INFORMATION: Synthetic Construct

<400> SEQUENCE: 28
cgcgaattca agcaccatag ttactgaaca                                             30
```